United States Patent [19]

Bathe et al.

[11] Patent Number: 5,699,790

[45] Date of Patent: Dec. 23, 1997

[54] SYSTEM FOR PREDICTING $NO_2$ CONCENTRATIONS

[75] Inventors: Duncan P. L. Bathe, Madison; Frederick J. Montgomery, Sun Prarie; Robin L. Roehl, Janesville, all of Wis.

[73] Assignee: Ohmeda Inc., Liberty Corner, N.J.

[21] Appl. No.: 620,063

[22] Filed: Mar. 21, 1996

[51] Int. Cl.[6] .................................................. A61M 11/00
[52] U.S. Cl. ........................ 128/204.22; 128/200.14; 128/203.12
[58] Field of Search .................... 128/200.14, 203.12, 128/204.21, 204.22, 204.23, 205.23

[56] References Cited

U.S. PATENT DOCUMENTS

| | | | |
|---|---|---|---|
| 4,402,315 | 9/1983 | Tsuda et al. | 128/203.12 |
| 4,473,536 | 9/1984 | Carberg et al. | |
| 4,546,794 | 10/1985 | Bail | 128/203.12 |
| 4,554,916 | 11/1985 | Watt | 128/203.12 |
| 4,602,653 | 7/1986 | Ruiz-Vela et al. | |
| 4,807,549 | 2/1989 | Lacey | |
| 4,860,223 | 8/1989 | Grilk | |
| 4,860,803 | 8/1989 | Wells | 128/204.22 |
| 5,046,018 | 9/1991 | Flewelling et al. | |
| 5,396,882 | 3/1995 | Zapol | 128/200.14 |
| 5,429,123 | 7/1995 | Zapol | |
| 5,485,827 | 1/1996 | Zapol | |
| 5,531,218 | 7/1996 | Krebs | 128/203.12 |
| 5,570,683 | 11/1996 | Zapol | 128/203.12 |

*Primary Examiner*—Vincent Millin
*Assistant Examiner*—William J. Deane, Jr.
*Attorney, Agent, or Firm*—Roger M. Rathbun; Salvatore P. Pace; R. Hain Swope

[57] ABSTRACT

A system and method for estimating the $NO_2$ concentration in the gas provided to a patient. The therapy of using nitric oxide to threat the lungs of a patient includes administering that gas along with a gas containing oxygen. Since the mixing of NO and oxygen cause a reaction leading to the formation of $NO_2$ and which is toxic, the method and system determine the concentration of oxygen in the oxygen containing gas, the concentration of NO in the NO containing gas and the residence time between the time those gasses are mixed together to the time that mixture is administered to the patient. Those values are then used, preferably in a microprocessor to access a look up table in the memory of the processor, to thereby provide an estimation of the $NO_2$ concentration of the gas administered to the patient.

20 Claims, 2 Drawing Sheets

SYSTEM FOR PREDICTING NO₂ CONCENTRATIONS

BACKGROUND OF THE INVENTION

This invention relates to the administration of inhaled nitric oxide to a patient by means of an administration apparatus and, more particularly, to a means of predicting the level of $NO_2$ that could be reached during that administration of that nitric oxide in any point of the system that may affect the patient.

Nitric oxide is generally administered to patients for various therapeutic reason, among them, the treating or preventing of bronchoconstriction or reversible pulmonary vasoconstriction. One of such treatments is the administration of NO by means of inhalation and the treatment is more fully set forth in U.S. Pat. No. 5,485,827 of The General Hospital Corporation.

To administer such NO, various apparatus have been used to provide the desired concentration to the patient. One such apparatus currently in use is with a mechanical ventilator having a known minute volume. The known concentration of NO is added to the volume of gas from the ventilator so that the final concentration of the NO in the mixture actually delivered to the patient is known.

One problem in the administration of NO is that it must, obviously be administered along with a life supporting amount or concentration of $O_2$ and therefore there must be, in effect, an administration of NO and $O_2$ and which mixture is then supplied to the patient.

The difficulty is that NO combines with $O_2$ to from $NO_2$ and which is toxic. It is understood that the reaction of NO and O2 to from $NO_2$ is time related, that is, the longer the contact of those components, the more $NO_2$ is formed in the mixture. Therefore, the period of time is critical between the contact of the NO and the $O_2$ and the time that mixture is actually introduced to the patient.

Accordingly it is therefore important that the actual mixture be made just prior to being administered to the patient. It cannot be mixed for storage in a tank and retained for future use.

Since the administration of NO could result in the formation of a toxic substance, it is therefore also very important to provide continuous and accurate monitoring of the $NO_2$ levels of the gas administered to the patient.

Currently there are $NO_2$ monitors in existence that do monitor the presence of that gas in the stream to a patient and are those monitors utilize electrochemical cells to detect the $NO_2$. However, in view of the criticality of the $NO_2$ level and the consequences of a high concentration of $NO_2$ present in the gas to the patient, it is useful to have a redundant technology that provides an independent measurement or prediction of the level of the $NO_2$ that can reach the patient.

SUMMARY OF THE INVENTION

In accordance with the present invention, there is provided a system for predicting the concentration of $NO_2$ that may reach the patient during the administration of inhaled nitric oxide that does not rely upon a conventional $NO_2$ monitor but utilizes different pieces of information concerning the NO gas administration apparatus and thus is a redundant system for determining $NO_2$ based on differing and independent technology than used in the conventional $NO_2$ monitors.

The present system of this invention provides a means of predicting the $NO_2$ concentration that could be reached in the gas administered to the patient and therefore adds an additional monitor that the user can have as assurance of the safety of the apparatus administering NO to the patient.

In carrying out the present invention, basically three parameters are obtained, either by calculation, estimation or other means and those three parameters are used to either carry out a theoretical algorithm to calculate the anticipated $NO_2$ concentrations or, alternatively, and as the preferred embodiment, the three parameters are used to access a three dimensional look up table stored in the data base of a CPU and which thus provides the estimated $NO_2$ concentration based on known relationships between those three parameters.

The three parameters are basically; the concentration of $O_2$ in the stream of gas to the patient, the concentration of NO in that stream and the determination of residence time of the gas as closely approximates the time between the time the NO and $O_2$ are mixed together to the time of introduction of those mixed NO and $O_2$ gases into the patient lungs.

The result is a prediction of the $NO_2$ concentration that can be reached in the patient and that prediction can be used to verify the reading of a $NO_2$ monitor as a redundant system, to provide an independent readout for information to the user or to activate an alarm when that predicted concentration reaches an unacceptable level.

Other objects, features and advantages of the present invention will be more apparent from the detailed description of the preferred embodiment set forth below, taken in conjunction with the accompanying drawings.

DESCRIPTION OF THE PREFERRED EMBODIMENT

Figure 1:
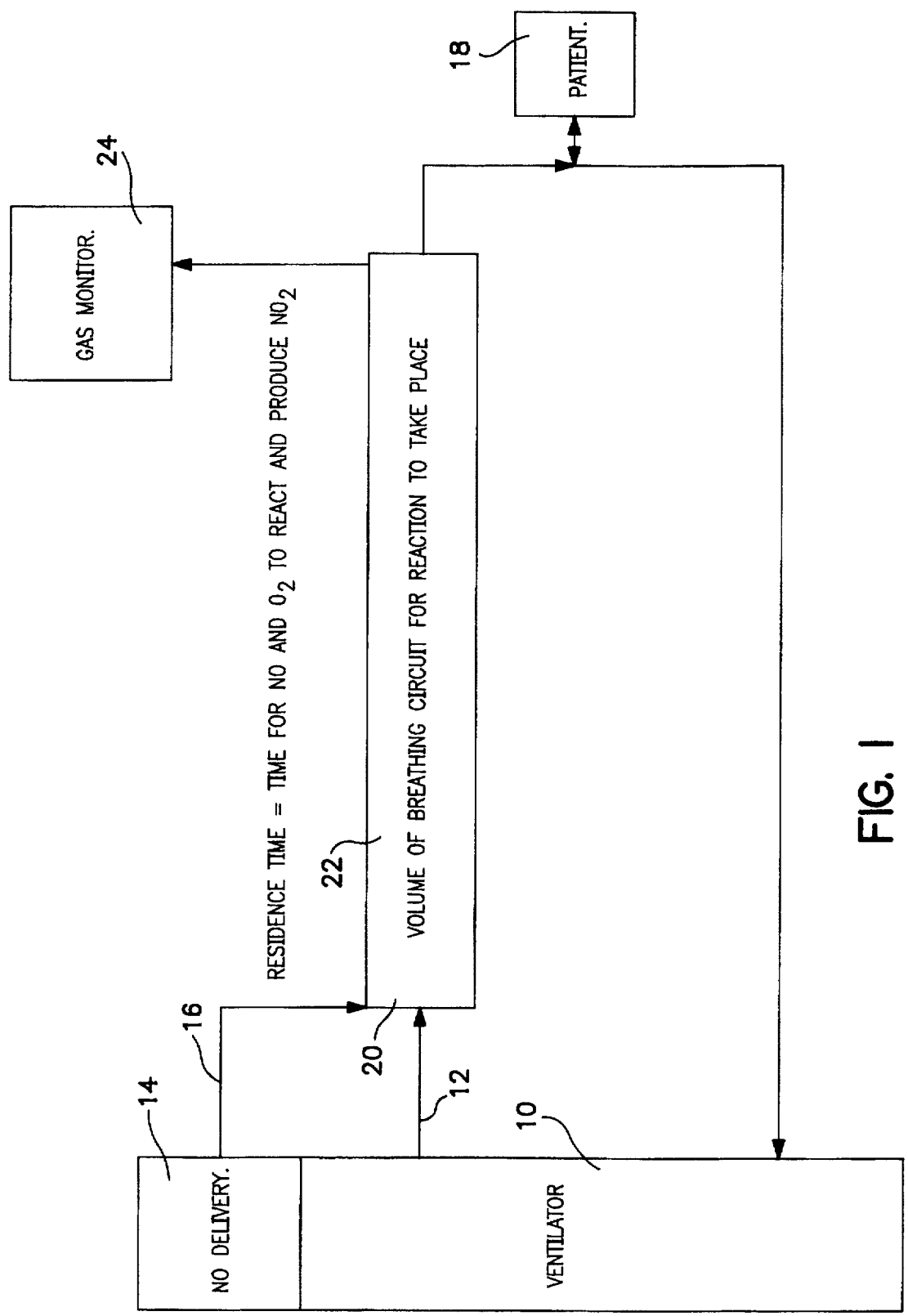
FIG. 1 is a block diagram of a typical system for providing inhaled nitric oxide to a patient.

Turning to FIG. 1, there is shown a block diagram of a typical system for providing inhaled nitric oxide to a patient. A ventilator 10 is provided and which produces a series of breaths to the patient to basically breathe for the patient.

A typical ventilator that may be used with the subject invention is shown and described in U.S. Pat. No. 5,315,989 of Tobia et al and assigned to the assignee of the present application. The disclosure of that U.S. patent is incorporated herein by reference. As shown in the FIG. 1, the outlet of the ventilator 10 may be through a tubing or conduit 12.

A nitric oxide delivery device 14 is also provided and which meters a precise amount of nitric oxide to be delivered to the patient. In current practice, the nitric oxide or NO is available commercially in cylinders and is normally mixed in another gas such as nitrogen. Typical concentrations of the gas cylinders may be in the range of 50 ppm to around 1000 ppm of NO in the nitrogen.

A typical system for metering the NO and providing the desired concentration of NO is shown and described in Applicant's copending published European Patent Application, Publication No. 0 659 445 A1, based upon a copending U.S. application of Bathe et al, now U.S. Pat. No. 5,558,083 issued Sep. 24, 1996 and assigned to the assignee of the present invention and the disclosure of that publication is incorporated herein by reference.

As may be noted in the aforementioned published Patent Application, the NO in the desired concentration flows through a conduit 16 and is mixed with the $O_2$ containing gas from the ventilator at the point 20 on FIG. 1.

At this point in time, since the NO is mixed with the $O_2$ in the gas from the ventilator, the NO begins to convert to $NO_2$ and from that point on, therefore, it is important that the mixture be administered to the patient 18 without significant delay since the formation of $NO_2$ is, as stated, toxic and is harmful to the patient.

Accordingly, the block 22 is designated to indicate the volume of passageways and the like that the mixture of NO and $O_2$ must pass on the way to the patient 18. That block, therefore represents various tubing, including the patient circuit that takes the mixture of NO and $O_2$ from the point of mixing at 20 to the actual introduction into the patient and is the critical path for the formation of $NO_2$.

Thus, in carrying out the administration of NO to the patient, it is important in estimating the amount of $NO_2$ that is formed between the point of mixing 20 and the introduction to the patient 18 to know the residence time of the mixture of NO and $O_2$ since that time is the determining factor in the reaction to produce $NO_2$.

Also, as shown in FIG. 1, a gas monitor 24 is normally provided in the commercial systems and which monitors $O_2$, $NO_2$ and NO in the stream to the patient 18. Although this monitor 24 is accurate and reliable, the use of the present $NO_2$ prediction means allows an entirely independent system for estimating the $NO_2$ and thus is a safety feature that provides a redundant system to back up the normal monitor 24 or to provide a continual check of the accuracy and viability of that monitor.

Figure 2:
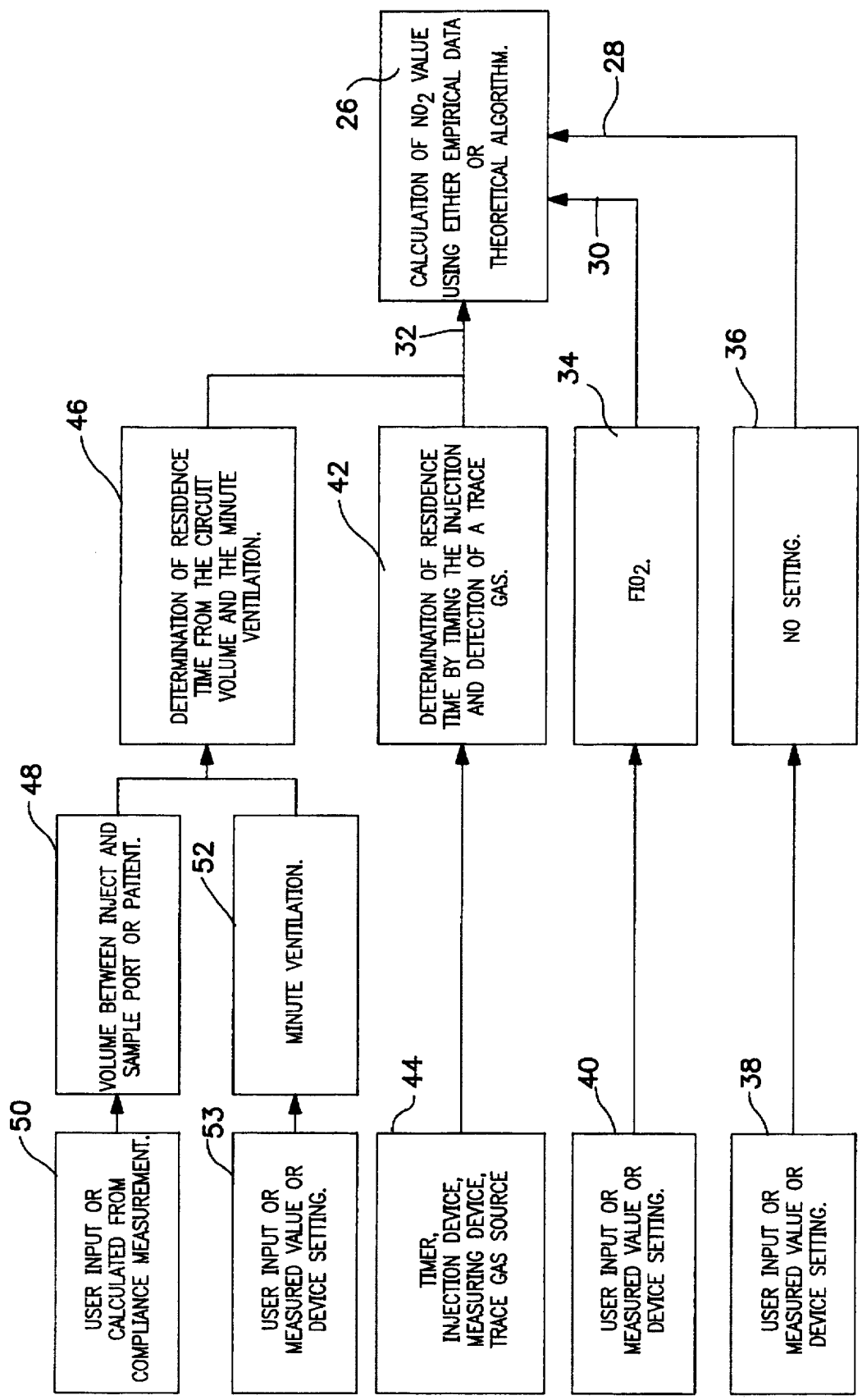
FIG. 2 is a block diagram of the steps in carrying out the present invention.

Turning now to FIG. 2, there is shown a block diagram of the various steps used in carrying out the present system for predicting the concentration of $NO_2$. The system utilizes a CPU 26 having in its memory, a three dimensional look up table for predicting $NO_2$ from three data inputs, that is, the NO concentration in the stream to the patient, the $O_2$ concentration in that same stream and a determination of the residence time between the time the NO is mixed with an O2 containing gas to the point the mixture of NO and $O_2$ is actually delivered to the patient.

The data in that look up input table is conveniently stored in ROM in the CPU 26 and the data itself can be gathered empirically from testing of the production of $NO_2$ in streams of mixtures of gasses containing $O_2$ and gases containing NO at varying concentrations within the general anticipated concentrations that are normally supplied to a patient.

For example, the NO concentrations may range from 0 ppm to about 80 ppm and the $O_2$ concentrations in gases from 21 to about 100 percent of oxygen. All of such data can be determined from testing at various residence times to arrive at a predicted $NO_2$ values in the ultimate stream of gas to the patient and that data presented in the three dimensional look up table in the CPU 26.

Alternatively, other than deriving the data empirically, the data can be derived by using the equation to determine the rate of change of the concentration of $NO_2$ i.e. $dC_{NO2}$ with respect to time dt according to the following:

$$dC_{NO2}/dt = kC^2_{NO}C_{O2}$$

where k is a rate constant determined by the system, C is the concentration of nitric oxide, $C_{O2}$ is the concentration of oxygen. Therefore the above equation may be used to calculate the predicted $NO_2$ concentration by use of the processor 26 as an alternative to the empirical method.

Accordingly, the CPU 26 only requires data input relating to NO concentration, $O_2$ concentration and the residence time of the mixture of the two components and can thus determine the predicted $NO_2$ concentration at the point that the stream of NO is administered to the patient.

Again, returning to FIG. 2, the inputs to the CPU 26 are shown as the NO concentration 28, the $O_2$ concentration 30 and the residence time 32 which is that time from when the gasses containing NO and $O_2$ are mixed together to the time that those mixed gases are administered to the patient.

Thus, the blocks 34 and 36, respectively, contain the data relating to $O_2$ concentration and NO concentration. The means of obtaining that data can vary, however, in the case of both the NO concentration and the O2 concentration, the data can be as shown by blocks 38 and 40 obtained by a user input or be some by a measurement of the gas streams or even by the device setting.

Accordingly, taking for example, the NO concentration, the data relating thereto may be input to the CPU 26 by means of the user inputting that data by a device such as a keyboard or the like. As an alternate, the NO concentration can be obtained by a dedicated monitor that determines the NO concentration in the stream of NO to the patient. Also, that concentration could be sent to the CPU 26 as the setting that the user determines at the NO delivery device. In any circumstance, the NO concentration that is in the stream of gas passing through block 22 of FIG. 1 is used as an input to the CPU as one of the data inputs.

As can be seen, the same means can be used to determine the data input for $O_2$ concentration as explained with respect to the NO input.

With respect to the residence time data, block 42 indicates the data obtained through one method of obtaining such data, that is, by the timing of an injection of a trace gas through the portion of the patient circuit as determined by that function of block 44. By this means, a trace gas is injected into the overall NO administration system and that trace gas is detected at a point downstream of the point of injection a predetermined distance. One of the trace gasses that can be used is NO itself.

Thus, the time of the travel of the trace gas is determined by timing the period of time that the trace gas is injected into the system to the time it is detected at the downstream location. Ideally, the injection can be made at the point where the NO containing gas is mixed with the gas containing O2 and the detection of that trace gas as close to the patient as possible such that the time determined from that procedure is close to the actual residence time of the NO and $O_2$ containing gas are mixed together and carried to the patient. As alternatives, however, a shorter or longer path may be timed and the actual residence time extrapolated from that data.

Another method of determining the residence time is shown as block 46 and the data is derived from a determination of the circuit volume and the minute ventilation. As shown, the data representative of the volume of the patient circuit may be derived as depicted in block 48 to be that volume that is present in the system between the where the NO and the gas containing $O_2$ are mixed and the point of administration to the patient.

That data, signified by block 50, can be obtained by means of the user inputting the data from the particular circuit being used, that is, the user knows which components are in the circuit and can either estimate the volume based on that knowledge or a table can be provided to the user specifying the various items in the circuit and the user can add up the total volume.

Alteratively the circuit volume may be determined by measuring the compliance in the circuit. Accordingly, that compliance can be calculated by passing a known volume of gas into the circuit and measuring the rise in pressure. With those values, the volume of the circuit $V_{CIRCUIT}$ is determined by the equation:

$$V_{CIRCUIT}=V_{MEASURED} \times P_{AMBIENT} + \Delta P_{MEASURED}$$

As to the minute volume of block 52, the input of this data can be by means of the user input, that is, some input device where the user inputs the information. Alternately, the data indicative of minute ventilation can be measured in the circuit through which the flow stream passes or, further, the data can be sent from a setting on the ventilator. Since many ventilators can now have that data set, i.e. the amount of flow the patient receives in a one minute period, it is easy for these actual settings on the ventilator to provide the data for this parameter.

In all, however, although the data representing the various inputs to the CPU 26 can be used, the inputs themselves are basically the $O_2$ concentration, the NO concentration and the residence time of the NO and $O_2$ from its point of mixing to the introduction into the patient. With this information, the CPU 26 can go to the look-up table provided in the CPU 26 to provide an estimate of the concentration of $NO_2$ in the stream of gas delivered to the patient or use the aforementioned equation to calculate the value.

While the present invention has been set forth in terms of a specific embodiment, it will be understood that the present system for predicting the $NO_2$ concentration in a gas stream to a patient herein disclosed may be modified or altered by those skilled in the art to other configurations. Accordingly, the invention is to be broadly construed and limited only by the scope and spirit of the claims appended hereto.

We claim:

1. A method of estimating the concentration of $NO_2$ in a mixture of NO and $O_2$ administered to a patient through a conduit, said method comprising:

(a) providing a supply of gas containing a known concentration of oxygen, (b) providing a supply of gas having a known concentration of nitric oxide, (c) mixing the NO containing gas and the $O_2$ containing gas in the conduit at a point prior to administration to the patient, (d) administering the mixed gas to a patient at a point downstream of the point of mixing the NO containing gas and the $O_2$ containing gas, (e) determining the time elapsed by the mixed gasses passing from the point of mixing the NO containing gas and the $O_2$ containing gas to the point the mixture is administered to the patient during which time $NO_2$ is formed in the mixture by the reaction of NO and $O_2$, and (f) using the NO concentration, the $O_2$ concentration and the time determined from step (e) to estimate the concentration of $NO_2$ in the mixed stream at the point it is administered to the patient.

2. A method as defined in claim 1 wherein said step of providing a supply of gas having a known concentration of $O_2$ comprises measuring the concentration of $O_2$ in said gas.

3. A method as defined in claim 1 wherein said step of providing a supply of gas having a known concentration of NO comprises measuring the concentration of NO in said gas.

4. A method as defined in claim 3 wherein said step of providing a supply of gas having a known concentration of $O_2$ comprises measuring the concentration of $O_2$ in said gas.

5. A method as defined in claim 1 wherein the step of determining the elapsed time comprises injecting a trace gas at a known position in the conduit, detecting that trace gas at a predetermined location downstream of the point of injection and calculating the elapsed time using the time and distance traveled by the trace gas.

6. A method as defined in claim 5 wherein the step of injecting a trace gas into the conduit comprises injecting NO as the trace gas.

7. A method of estimating the concentration of $NO_2$ in a mixture of NO and $O_2$ administered to a patient, said method comprising:

(a) providing a supply of gas containing a known concentration of oxygen, (b) providing a supply of gas having a known concentration of nitric oxide, (c) providing a ventilator controllable by a processor and having a means to set the minute volume of gas to be delivered to the patient, (d) mixing the NO containing gas and the $O_2$ containing gas in a confluence prior to introduction to the patient by the ventilator, (e) administering the mixed gas to a patient at a point downstream of the confluence, (f) determining the time elapsed by the mixed gases from the confluence where the NO containing gas and the $O_2$ containing gasses are mixed to the point the mixture is administered to the patient during which time $NO_2$ is formed in the mixed gases by the reaction of NO and $O_2$, and (g) using the NO concentration, the $O_2$ concentration and the time determined from step (f) to determine from data stored in the processor of the concentration of $NO_2$ in the mixed stream at the point it is administered to the patient.

8. A method as defined in claim 7 wherein the step of determining the elapsed time includes calculating the elapsed time in the processor using the minute volume set by the user.

9. A method as defined in claim 7 wherein the step of determining the elapsed time includes measuring the minute volume delivered by the ventilator.

10. A method as defined in claim 7 wherein the step of determining the elapsed time includes measuring the volume in the conduit between point of mixing and point of introduction to the patient.

11. A method as defined in claim 7 wherein the step of determining residence time includes the step of determining the set minute volume to be delivered to the patient.

12. A method as defined in claim 11 wherein the step of determining the elapsed time includes calculating the volume in the conduit to the patient from the confluence by measuring the compliance in the conduit.

13. A system for estimating the concentration of $NO_2$ in a mixture of NO and $O_2$ administered to a patient, said system comprising a ventilator for providing a supply of gas containing a known concentration of oxygen, conduit means for conducting said $O_2$ containing gas from said ventilator to a point where the gas is administered to the patient, a supply of a gas having a known concentration of nitric oxide, means for mixing the NO containing gas and the $O_2$ containing gas within said conduit at a point intermediate said ventilator and the patient, means for measuring the elapsed time of the mixed gas from the point of mixing the NO containing gas and the $O_2$ containing gas to the point the mixture is administered to the patient during which time $NO_2$ is formed in the mixture by the reaction of NO and $O_2$, and processor means receiving as inputs, the NO concentration, the $O_2$ concentration and the elapsed time to determine the estimated concentration of $NO_2$ in the mixed stream administered to the patient.

14. A system for estimating the concentration of $NO_2$ in a mixture of NO and $O_2$ administered to a patient as defined in claim 13 wherein said processor means is a microprocessor having a three dimensional look up table in memory to determine the estimated concentration of $NO_2$.

15. A system for estimating the concentration of $NO_2$ in a mixture of NO and $O_2$ administered to a patient as defined in claim 13 wherein said processor means calculates the concentration based on the follow equation:

$$dC_{NO2}/dt = kC^2_{NO}C_{O2}.$$

16. A system for estimating the concentration of $NO_2$ in a mixture of NO and $O_2$ administered to a patient as defined in claim 13 further including an $O_2$ sensor and a NO sensor to determine the concentration of $O_2$ and NO in the supplies of $O_2$ and NO.

17. A system for estimating the concentration of $NO_2$ in a mixture of NO and $O_2$ administered to a patient as defined in claim 13 wherein said means for measuring the elapsed time comprises an injector for injecting a trace gas into said conduit at an injection point and a detector for detecting the presence of the trace gas at a known distance downstream from said injection point.

18. A system for estimating the concentration of $NO_2$ in a mixture of NO and $O_2$ administered to a patient as defined in claim 13 wherein said ventilator is settable by a user to deliver a certain minute volume, and means to provide the value of such setting to said processor for use in estimating the $NO_2$ concentration.

19. A system for estimating the concentration of $NO_2$ in a mixture of NO and $O_2$ administered to a patient as defined in claim 13 further comprising means to inject a trace gas into said conduit means, means to detect said trace gas at a predetermined point downstream in said conduit, means to time the trace gas from point of injection to point of detection and wherein said processor calculates the residence time based upon the means to time the trace gas.

20. A system for estimating the concentration of $NO_2$ in a mixture of NO and $O_2$ administered to a patient as defined in claim 19 wherein said trace gas is nitric oxide.

* * * * *